United States Patent
Onodera

(10) Patent No.: US 11,826,928 B2
(45) Date of Patent: Nov. 28, 2023

(54) QUALITY INSPECTION METHOD AND QUALITY INSPECTION SYSTEM FOR UNVULCANIZED RUBBER MATERIAL, AND PRODUCTION METHOD AND PRODUCTION SYSTEM FOR UNVULCANIZED RUBBER MATERIAL

(71) Applicant: The Yokohama Rubber Co., LTD., Tokyo (JP)

(72) Inventor: Satoshi Onodera, Hiratsuka (JP)

(73) Assignee: The Yokohama Rubber Co., LTD., Tokyo (JP)

( * ) Notice: Subject to any disclaimer, the term of this patent is extended or adjusted under 35 U.S.C. 154(b) by 582 days.

(21) Appl. No.: 16/770,934

(22) PCT Filed: Sep. 26, 2018

(86) PCT No.: PCT/JP2018/035774
§ 371 (c)(1),
(2) Date: Jun. 8, 2020

(87) PCT Pub. No.: WO2019/111500
PCT Pub. Date: Jun. 13, 2019

(65) Prior Publication Data
US 2021/0162632 A1    Jun. 3, 2021

(30) Foreign Application Priority Data

Dec. 8, 2017  (JP) ................................ 2017-236178
Dec. 8, 2017  (JP) ................................ 2017-236179

(51) Int. Cl.
| | | |
|---|---|---|
| *B29B 7/42* | (2006.01) | |
| *B29B 7/72* | (2006.01) | |
| *B29B 7/00* | (2006.01) | |
| *B29B 7/90* | (2006.01) | |
| *C08J 3/20* | (2006.01) | |
| *G01N 29/04* | (2006.01) | |
| *G01N 33/44* | (2006.01) | |
| *B29K 21/00* | (2006.01) | |
| *B29K 105/00* | (2006.01) | |
| *B29K 105/24* | (2006.01) | |
| *B29K 507/04* | (2006.01) | |
| *B29K 509/08* | (2006.01) | |

(52) U.S. Cl.
CPC .............. *B29B 7/726* (2013.01); *B29B 7/007* (2013.01); *B29B 7/42* (2013.01); *B29B 7/90* (2013.01); *C08J 3/203* (2013.01); *G01N 29/04* (2013.01); *G01N 33/445* (2013.01); *B29K 2021/006* (2013.01); *B29K 2105/0005* (2013.01); *B29K 2105/246* (2013.01); *B29K 2507/04* (2013.01); *B29K 2509/08* (2013.01); *C08J 2321/00* (2013.01); *C08J 2421/00* (2013.01); *G01N 2291/0235* (2013.01); *G01N 2291/02863* (2013.01)

(58) Field of Classification Search
CPC .......... B29B 7/726; B29B 7/007; B29B 7/42; B29B 7/90; B29B 7/60; B29B 7/7466; B29B 7/748; B29B 7/7485; B29B 7/7495; C08J 3/203; C08J 2321/00; C08J 2421/00; C08J 2321/02; G01N 29/04; G01N 33/445; G01N 2291/0235; G01N 2291/02863; B29K 2021/006; B29K 2105/0005; B29K 2105/246; B29K 2507/04; B29K 2509/08; B29C 2948/92238; B29C 2948/92447; B29C 48/92; B29C 7/426
USPC ....................................................... 366/76.2
See application file for complete search history.

(56) References Cited

U.S. PATENT DOCUMENTS

2013/0153110 A1* 6/2013 Miyazaki ................. C08L 9/00
                                                            524/398
2014/0366633 A1   12/2014 Schroeder et al.

FOREIGN PATENT DOCUMENTS

| JP | 2005-001228 | 1/2005 |
|---|---|---|
| JP | 2006-214941 | 8/2006 |
| JP | 2014-521948 | 8/2014 |
| WO | WO 2007/137404 | 12/2007 |
| WO | WO 2013/014270 | 1/2013 |

OTHER PUBLICATIONS

International Search Report for International Application No. PCT/JP2018/035774 dated Dec. 11, 2018, 2 pages, Japan.
Shujiro Shiga et al., Possibility of Mixing Level Estimation Using Dielectric Constant, Journal of the Society of Rubber Science and Technology, 1995, vol. 68, No. 3, pp. 193-196, 5 pages, Japan.

* cited by examiner

*Primary Examiner* — Hannah J Pak
(74) *Attorney, Agent, or Firm* — Thorpe North & Western

(57) ABSTRACT

Provided are a quality inspection method and a quality inspection system for unvulcanized rubber material. A final dielectric constant measurement device detects the dielectric constant of a final rubber material in which a compounding agent of predetermined type is mixed with unvulcanized rubber, and a calculator calculates a compounding ratio of the compounding agent to the final rubber material based on the detected dielectric constant, determines whether or not the calculated compounding ratio is in a preset compounding reference range, displays a determination result on a monitor, and adjusts a ratio of the compounding agent fed into an extruder to the unvulcanized rubber such that the calculated compounding ratio is within the compounding reference range.

5 Claims, 6 Drawing Sheets

QUALITY INSPECTION METHOD AND QUALITY INSPECTION SYSTEM FOR UNVULCANIZED RUBBER MATERIAL, AND PRODUCTION METHOD AND PRODUCTION SYSTEM FOR UNVULCANIZED RUBBER MATERIAL

TECHNICAL FIELD

The present technology relates to a quality inspection method and a quality inspection system for unvulcanized rubber material, and a production method and a production system for unvulcanized rubber material.

BACKGROUND ART

Producing a rubber product such as a tire or the like includes a step of kneading an unvulcanized rubber and a compounding agent using a mixer (mixing machine) or a rubber extruder to produce an unvulcanized rubber material. In this production step, the compounding agent is added at a compounding ratio set for the unvulcanized rubber. If the compounding ratio of the actually added compounding agent deviates from the reference range, the quality of the produced unvulcanized rubber material will be affected. This also affects the quality of the rubber product produced using this unvulcanized rubber material.

An oxygen flask combustion method or a sodium peroxide melting method have been are known as methods for inspecting the compounded amount of sulfur in an unvulcanized rubber material. However, in these inspection methods, procedures and preparations are complex, and time required for inspection is long. In addition, these inspection methods require complicated procedures and preparations and cannot perform inspection on the production line for the unvulcanized rubber material, failing to produce the unvulcanized rubber material of predetermined quality with good productivity.

As a method for determining the quality of an unvulcanized rubber material, a method has been proposed in which ultrasonic waves (0.5 MHz to 20 MHz) are transmitted to the extruded unvulcanized rubber material, and an attenuation amount of the strength of the ultrasonic waves transmitted through the unvulcanized rubber material (see Japan Unexamined Patent Publication No. 2014-521948). The proposed method can recognize the presence or absence of contaminants in the unvulcanized rubber material, and the relative change in the content of the contaminants on the basis of the attenuation amount of the strength of the ultrasonic waves, but does not determine whether or not the compounding ratio of the compounding agent in the unvulcanized rubber material is appropriate.

A method for measuring the concentration, the content rate, and the like of the chloride in concrete, although not unvulcanized rubber material, has been known (for example, see Japan Unexamined Patent Publication No. 2006-214941).

SUMMARY

The present technology provides a quality inspection method and a quality inspection system for unvulcanized rubber material that can easily and quickly determine the acceptability of the compounding ratio of a compounding agent in the unvulcanized rubber material. Another object of the present technology is to provide a production method and a production system for unvulcanized rubber material that can produce the unvulcanized rubber material on the production line for the unvulcanized rubber material with good productivity, with a compounding agent of predetermined type being mixed with unvulcanized rubber at an appropriate compounding ratio.

A quality inspection method for unvulcanized rubber material according to the present technology includes: based on a dielectric constant of an unvulcanized rubber material in which a compounding agent of predetermined type is mixed with unvulcanized rubber, calculating a compounding ratio of the compounding agent to the unvulcanized rubber material by a calculator; and determining whether or not the calculated compounding ratio is within a preset compounding reference range by the calculator.

A quality inspection system for unvulcanized rubber material according to the present technology including:
  a dielectric constant measurement device configured to detect a dielectric constant of an unvulcanized rubber material obtained by mixing a compounding agent of predetermined type to unvulcanized rubber; and
  a calculator configured to receive an input of the dielectric constant detected by the dielectric constant measurement device, wherein
  the calculator calculates a compounding ratio of the compounding agent in the unvulcanized rubber material based on the dielectric constant, and determines whether or not the calculated compounding ratio is within a compounding reference range input to the calculator.

According to the present technology, a production method for unvulcanized rubber material for feeding a primary rubber material that is a mixture of unvulcanized rubber and an unvulcanizing compounding agent of predetermined type, and a vulcanizing compounding agent of predetermined type into an extruder, and perform mixing to continuously produce a final rubber material includes: calculating a compounding ratio of the vulcanizing compounding agent to the final rubber material by a final calculator based on a dielectric constant of the final rubber material extruded from the extruder; and adjusting a ratio of the vulcanizing compounding agent fed to the extruder to the unvulcanized rubber such that the calculated compounding ratio is within a preset vulcanizing compounding reference range.

A production system for unvulcanized rubber material according to the present technology includes: an extruder configured to mix a primary rubber material that is a mixture of unvulcanized rubber and an unvulcanizing compounding agent of predetermined type, and a vulcanizing compounding agent of predetermined type, and extrude a final rubber material; a vulcanizing compounding agent supply unit configured to feed the vulcanizing compounding agent into the extruder; a final dielectric constant measurement device configured to detect a dielectric constant of the final rubber material; a final calculator configured to receive an input of the dielectric constant detected by the final dielectric constant measurement device; and a final controller configured to control the vulcanizing compounding agent supply unit, wherein a compounding ratio of the vulcanizing compounding agent to the final rubber material is calculated by the final calculator based on the dielectric constant, the vulcanizing compounding agent supply unit is controlled by the final controller based on comparison of the calculated compounding ratio and a preset vulcanizing compounding reference range, and a ratio of the vulcanizing compounding agent fed to the extruder to the unvulcanized rubber is adjusted such that the compounding ratio calculated by the final calculator is within the vulcanizing compounding reference range.

In the quality inspection method and the quality inspection system for the unvulcanized rubber material according to the present technology, by detecting the dielectric constant of the unvulcanized rubber material, and performing calculation based on the dielectric constant by the calculator, the compounding ratio of the compounding agent of the unvulcanized rubber material may be calculated to rapidly determine the acceptability of the compounding ratio. Moreover, since it is no need to acquire data using various solutions, inspection may be easily performed.

In the production method and the production system for unvulcanized rubber material according to the present technology, by detecting the dielectric constant of the final rubber material extruded from the extruder, and performing calculation based on the dielectric constant by the final calculator, the compounding ratio of the vulcanizing compounding agent to the final rubber material may be calculated to determine the acceptability of the compounding ratio easily and rapidly. Therefore, by adjusting the ratio of the vulcanizing compounding agent fed to the extruder to the unvulcanized rubber based on the determination result, it is possible to acquire an unvulcanized rubber material in which the vulcanizing compounding agent is mixed with the unvulcanized rubber at an appropriate compounding ratio within the vulcanizing compounding reference range. Moreover, since the acceptability of the compounding ratio may be determined on the production line of the unvulcanized rubber material, the unvulcanized rubber material of predetermined quality may be produced with good productivity.

DETAILED DESCRIPTION

A quality inspection method and a quality inspection system for unvulcanized rubber material according to the present technology will be described below based on the illustrated embodiments.

Figure 1:
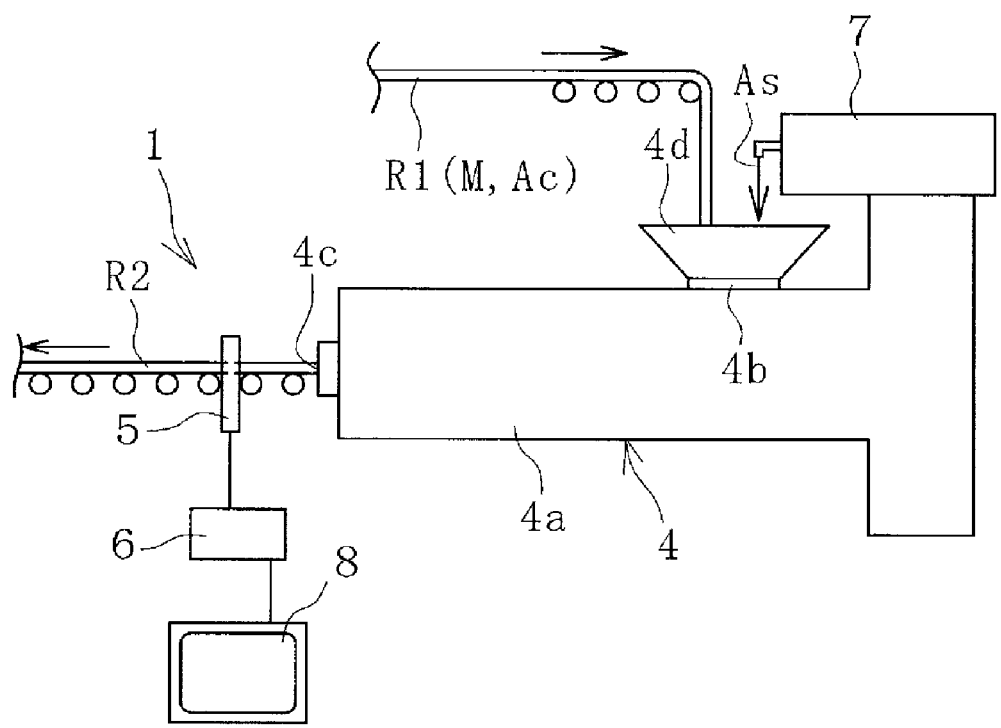
FIG. 1 is an explanatory diagram illustrating a quality inspection system for unvulcanized rubber material according to the present technology.

A quality inspection system 1 for unvulcanized rubber material (hereinafter referred to as the inspection system 1) according to the present technology in FIG. 1 includes a dielectric constant measurement device 5, a calculator 6 that receives an input of the dielectric constant detected by the dielectric constant measurement device 5, and a monitor 8 connected to the calculator 6 in a wired or wireless manner.

The present technology may inspect, as an unvulcanized rubber material R, both a primary rubber material R1 in which an unvulcanized rubber M and an unvulcanizing compounding agent Ac of predetermined type are mixed, and a final rubber materials R2 in which the primary rubber material R1 and a vulcanizing compounding agent As of predetermined type are mixed. In this embodiment, the final rubber material R2 just extruded by the extruder 4 is used as the inspection target.

Examples of the unvulcanizing compounding agent Ac include carbon black and silica. Examples of the vulcanizing compounding agent As include at least one of a vulcanization activator, a vulcanization accelerator, and sulfur. A master batch in which the vulcanization activator, the vulcanization accelerator, and the sulfur are mixed at prescribed ratios may be used as the vulcanizing compounding agent As.

An extruder 4 includes a cylinder 4a provided with a rotationally-driven screw, a material feeding port 4b formed on a top surface of a rear end of the cylinder 4a, a hopper 4d disposed on the material feeding port 4b, and an extrusion port 4c formed on the tip of the cylinder 4a. A conveyance means such as a conveyor extends in front of the extrusion port 4c. Additionally, a compounding agent supply unit 7 that feeds the vulcanizing compounding agent As of predetermined type to the material feeding port 4b via the hopper 4d is provided.

A sheet-like primary rubber material R1 is continuously fed into the cylinder 4a of the extruder 4 from the material feeding port 4b via the hopper 4d. In addition, the vulcanizing compounding agent As of predetermined type is continuously fed from the material feeding port 4b via the hopper 4d by the compounding agent supply unit 7. The vulcanizing compounding agent As is set to be fed at a predetermined ratio preset for 100 weight parts of the unvulcanized rubber M.

The fed primary rubber material R1 and the vulcanizing compounding agent As move forward while being mixed and kneaded in the cylinder 4a by the rotating screw. Then, the final rubber material R2 formed into a sheet form is continuously extruded from the extrusion port 4c.

The dielectric constant measurement device 5 may use equipment various known specifications. Preferable equipment is capable of irradiating the inspection target (unvulcanized rubber material R) with ultrasonic waves and detecting the dielectric constant in a non-contact manner. For example, the dielectric constant measurement device 5 sequentially detects the dielectric constant in the range through which the final rubber material R2 passes while being extruded.

Not only a single but a plurality of dielectric constant measurement devices 5 may be aligned in the width direction of the final rubber material R2. Alternatively, the dielectric constant measurement device 5 may be configured to be movable in the width direction of the final rubber material R2. By employing these configurations, the substantially entire width of the final rubber material R2 can be inspected.

Figure 2:
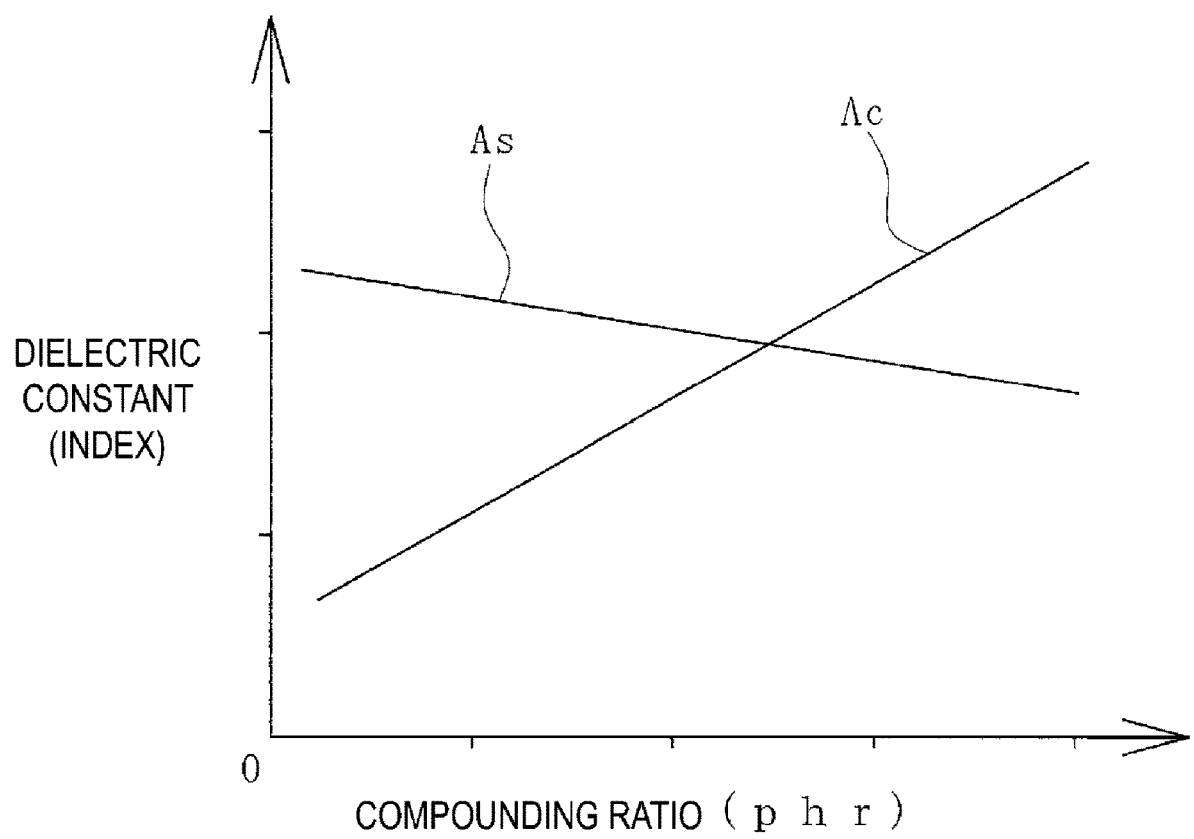
FIG. 2 is a graph schematically illustrating the relationship between each of the compounding ratio of carbon black and the compounding ratio of a master batch and the dielectric constant of the unvulcanized rubber material.

As illustrated in FIG. 2, correlation data between the compounding ratio of the vulcanizing compounding agent As of predetermined type in the final rubber material R2 and the dielectric constant of the final rubber material R2 are input to the calculator 6. Specifically, as the compounding ratio of the master batch used as the vulcanizing compounding agent As increases, the dielectric constant of the final rubber material R2 tends to decrease. The calculator 6 calculates a compounding ratio D1 of the vulcanizing compounding agent As in the final rubber material R2 on the basis of the correlation data and the sequentially-input dielectric constant.

In this embodiment, correlation data between the compounding ratio of the unvulcanizing compounding agent Ac of predetermined type in the primary rubber material R1 and the dielectric constant of the primary rubber material R1 is also input to the calculator 6. Specifically, as the compounding ratio of carbon black used as the unvulcanizing compounding agent Ac increases, the dielectric constant of the primary rubber material R1 tends to increase. According to the type of the compounding agents A (Ac, As), the correlation between the compounding ratio and the dielectric constant of the unvulcanized rubber material R mixed with the compounding agent A (which the dielectric constant increases or decreases proportionally, the degree of change in the dielectric constant) varies, and therefore, for each compounding agent A, the correlation data is previously acquired and input to the calculator 6.

Figure 3:
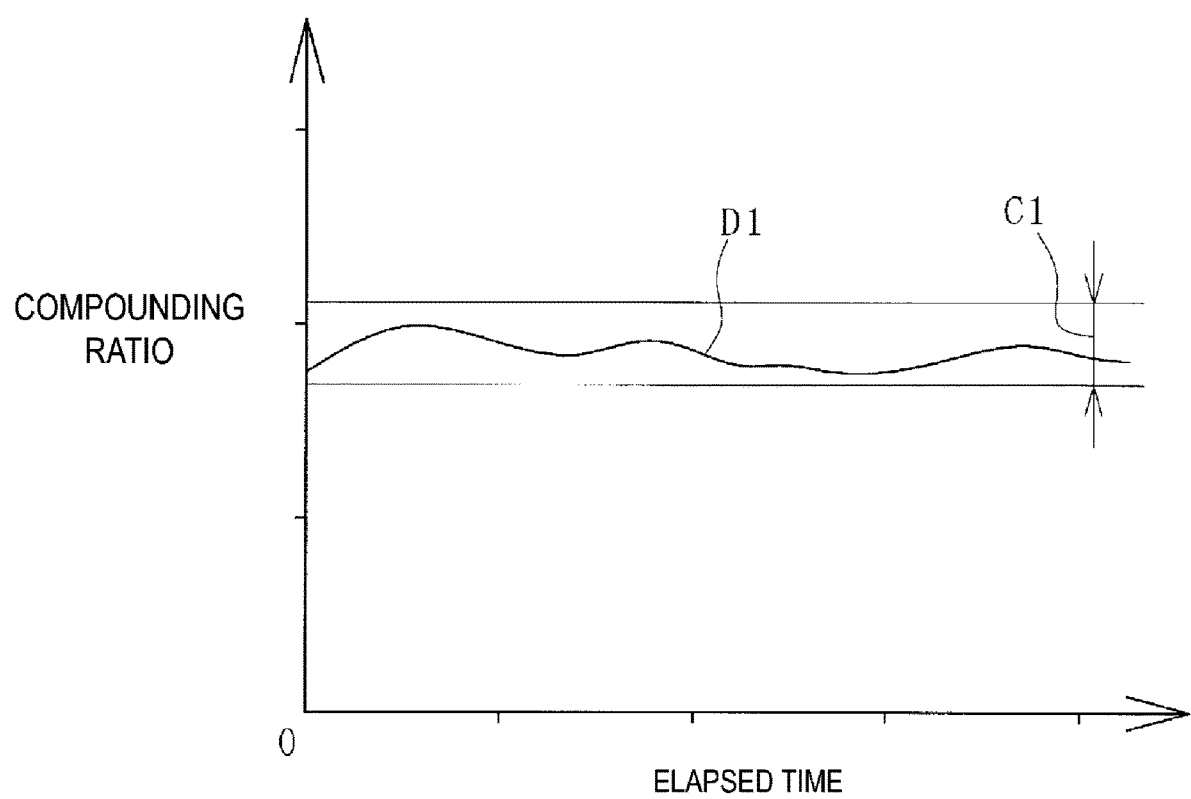
FIG. 3 is an explanatory diagram illustrating contents (change in the compounding ratio of the compounding agent over time) displayed on a monitor.

A compounding reference range C1 indicating the appropriate compounding ratio for each type of the vulcanizing compounding agent As is also input to the calculator 6. As illustrated in FIG. 3, the calculator 6 sequentially compares the calculated compounding ratio D1 with the compounding reference range C1, and sequentially determines whether or not the compounding ratio D1 is within the compounding reference range C1.

The determination result of the calculator 6 is sequentially displayed on the monitor 8. The displayed determination result may be a warning simply indicating that the calculated compounding ratio D1 is out of the range of the compounding reference range C1, or a change in the compounding ratio D1 over time illustrated in FIG. 3 may be sequentially displayed.

As described above, according to the present technology, by detecting the dielectric constant of the final rubber material R2 and performing calculation based on the dielectric constant to calculate the compounding ratio of the vulcanizing compounding agent As in the final rubber material R2, the acceptability of the compounding ratio can be rapidly determined by the non-destructive inspection. Moreover, unlike the known inspection method, there is no need to acquire data using various solutions, achieving simple inspection.

Even when the vulcanizing compounding agent As is added to the primary rubber material R1 at a compounding ratio within the compounding reference range C1, unless the vulcanizing compounding agent As is sufficiently dispersed and mixed with the unvulcanized rubber M (primary rubber material R1), the quality of the final rubber material R2 produced is disadvantageously affected. Therefore, it is more preferable to determine the acceptability of the dispersion of the vulcanizing compounding agent As as well.

Thus, the extruded final rubber material R2 is divided into multiple segments in a plan view, and the dielectric constant is detected for each divided segment. Then, based on the magnitude of a variation in the detected dielectric constants of the segments, the calculator 6 calculates a degree of dispersion D2 of the vulcanizing compounding agent As in the final rubber material R2.

A dispersion reference range C2 indicating the appropriate degree of dispersion D2 for each type of the vulcanizing compounding agent As is input to the calculator 6. Then, the calculator 6 sequentially compares the calculated degree of dispersion D2 with the dispersion reference range C2, and determines whether or not the degree of dispersion D2 is within the dispersion reference range C2.

For example, a reference dielectric constant Cd is set, and a value acquired by averaging absolute values of differences between the reference dielectric constant Cd and the dielectric constants of the segments in a predetermined area range (per unit area) is defined as the degree of dispersion D2. As the degree of dispersion D2 is larger, dispersion of the vulcanizing compounding agent As becomes worse, and thus, a preset average allowable range is previously set to the dispersion reference range C2, and it is determined that the dispersion is poor when the degree of dispersion D2 is greater than the dispersion reference range C2.

Also when the dielectric constant is locally too large or too small, it can be deemed that the vulcanizing compounding agent As is not well dispersed. Thus, a preset local allowable range is set to the dispersion reference range C2, and it may be determined that the dispersion is poor when a segment where the degree of dispersion D2 is larger than the dispersion reference range C2 is present. At least one of the above-mentioned average allowable range and local allowable range may be adopted as the dispersion reference range C2, but both are preferably adopted.

The determination result of the calculator 6 is sequentially displayed on the monitor 8. The displayed determination result may be a warning that simply indicates that the calculated degree of dispersion D2 is outside the range of the dispersion reference range C2, but as illustrated in FIG. 4, the dispersion of the dielectric constant (or the compounding ratio D1) may be displayed.

Figure 4:
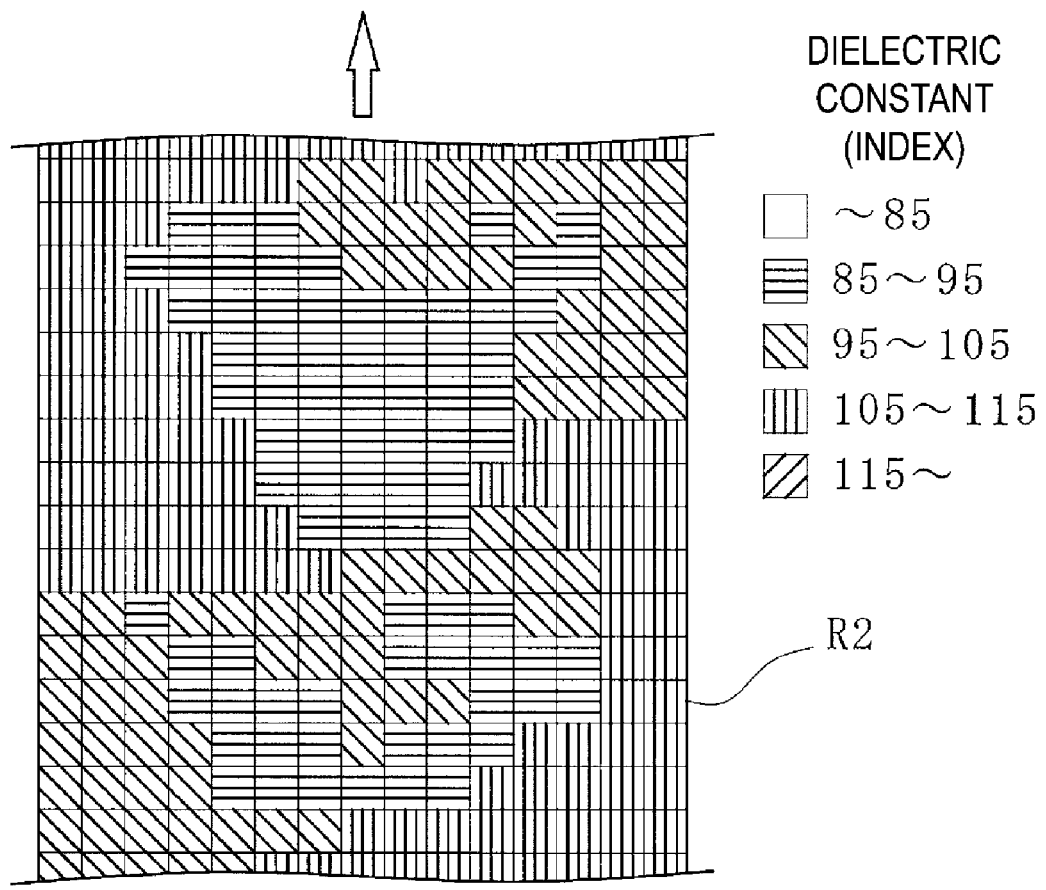
FIG. 4 is an explanatory diagram illustrating another type of contents (the dispersion of the compounding agent) displayed on a monitor.

In displaying as illustrated in FIG. 4, the segments are categorized into a plurality of ranks (for example, an index such as less than 85, 85 to 95, . . . ) by the calculator 6 according to the magnitude of the dielectric constant. Each segment is then displayed on the monitor 8 such that its rank is distinguishable. In FIG. 4, the categorized ranks are distinguishable using blank and line patterns, but may be distinguishable using the difference in color or shade of color. With such display, the acceptability of the dispersion of the vulcanizing compounding agent As may be easily recognized by simply looking at the monitor 8.

The contents described above may be applied to the primary rubber material R1 as well. In other words, by detecting the dielectric constant of the primary rubber material R1 and performing calculation based on the dielectric constant, the compounding ratio of the unvulcanizing compounding agent Ac in the primary rubber material R1 and the acceptability of the compounding ratio may be rapidly determined. Additionally, the acceptability of the dispersion of the unvulcanizing compounding agent Ac in the primary rubber material R1 may be determined in the same manner as in the final rubber material R2.

Next, a production method and a production system for unvulcanized rubber material according to the present technology will be described with reference to the illustrated embodiment.

Figure 5:
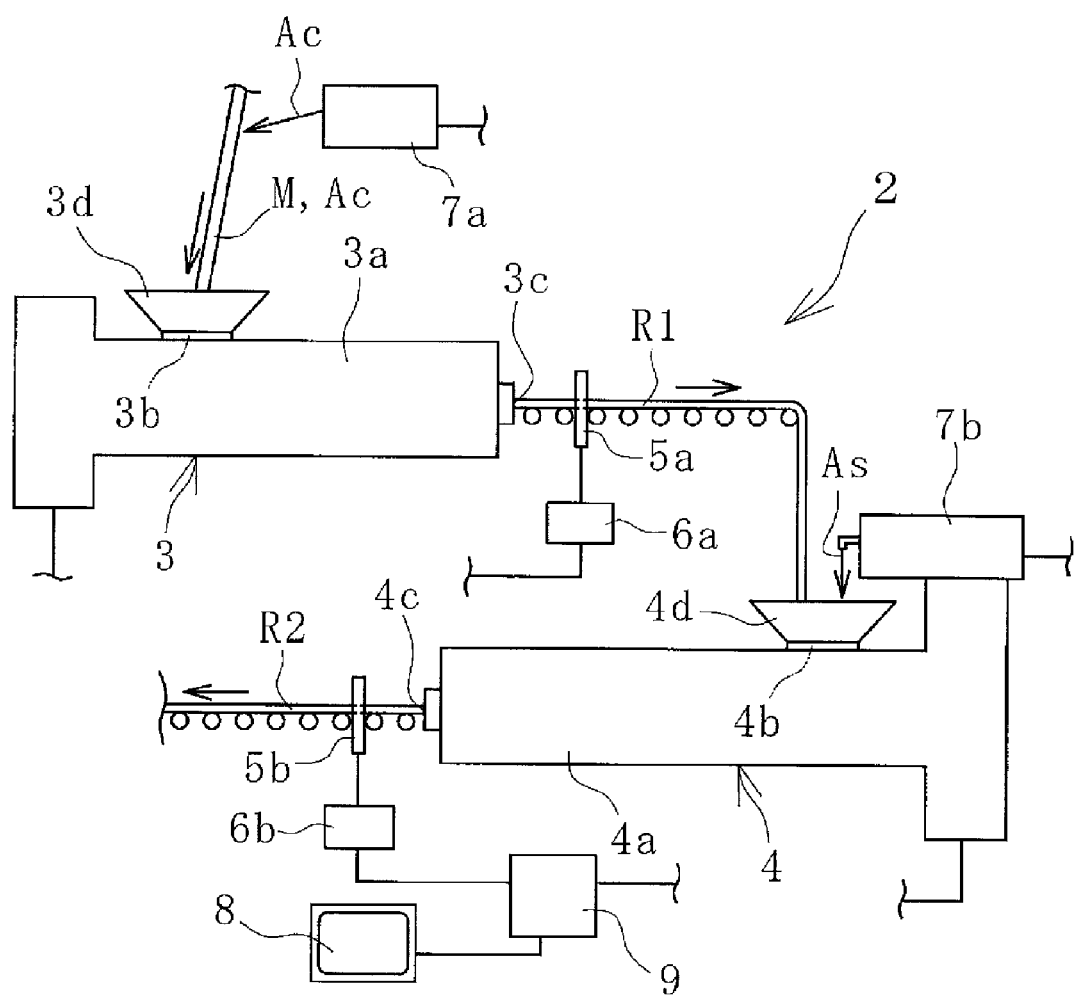
FIG. 5 is an explanatory diagram illustrating a production system for unvulcanized rubber material according to the present technology.
Figure 6:
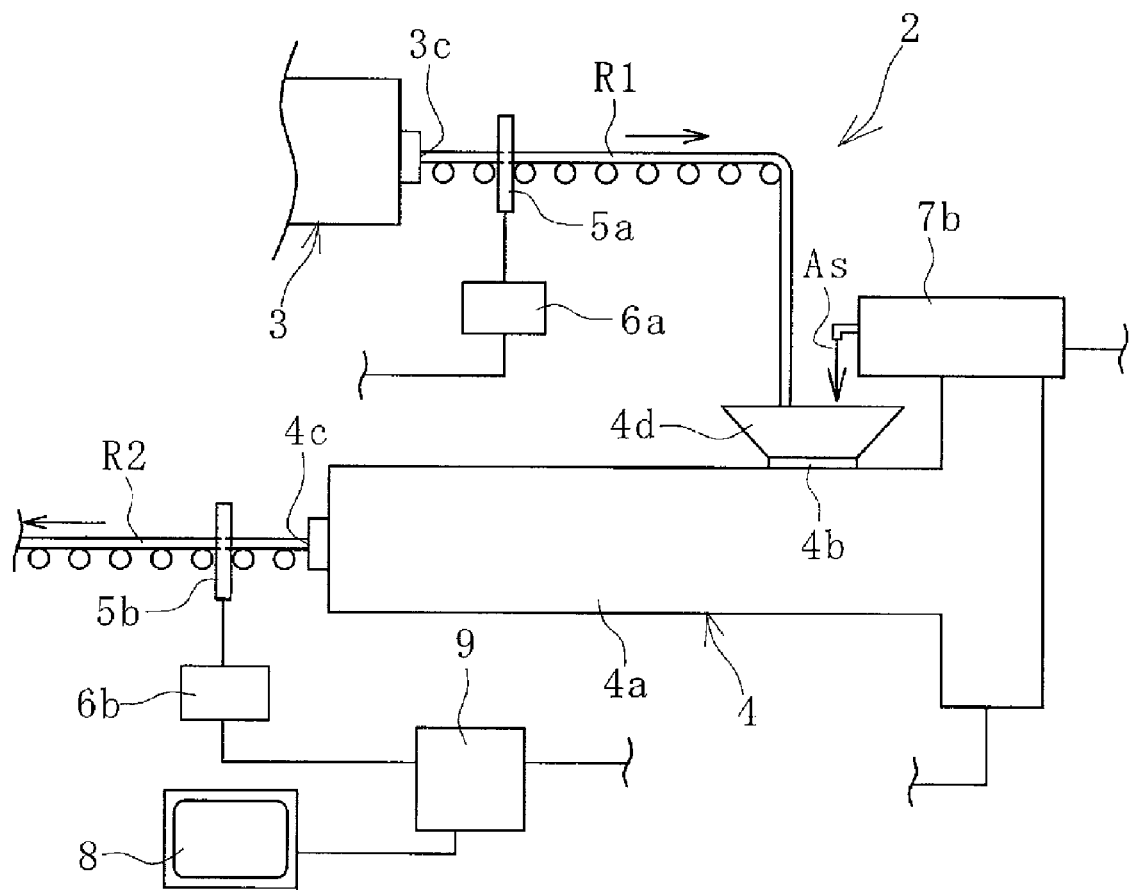
FIG. 6 is a partial enlarged diagram illustrating the production system of FIG. 5.

A production system 2 for unvulcanized rubber material (hereinafter referred to as production system 2) according to the present technology illustrated in FIGS. 5 and 6 utilizes the above-described inspection system 1 according to the present technology. The production system 2 includes an extruder 4 that extrudes the final rubber material R2, a vulcanizing compounding agent supply unit 7b that feeds the vulcanizing compounding agent As into the extruder 4, a final dielectric constant measurement device 5b, a final calculator 6b that receives an input of the dielectric constant detected by the final dielectric constant measurement device 5b, and a final controller 9 that controls the vulcanizing compounding agent supply unit 7b. The final dielectric constant measurement device 5b is intended to inspect the final rubber material R2 just extruded by the extruder 4. The final rubber material R2 is formed by mixing the primary rubber material R1 and the vulcanizing compounding agent As of predetermined type, and the primary rubber material R1 is formed by mixing unvulcanized rubber M and the unvulcanizing compounding agent Ac of predetermined type. The final calculator 6b is connected to the final controller 9 in a wired or wireless manner.

The production system 2 in the embodiment includes equipment for the primary rubber material R1, which is similar to the above-mentioned equipment for the final rubber material R2. Specifically, the production system includes an extruder 3 that extrudes the primary rubber material R1, an unvulcanizing compounding agent supply unit 7a that feeds the unvulcanizing compounding agent Ac into the extruder 3, a primary dielectric constant measurement device 5a, a primary calculator 6a that receives an input of the dielectric constant detected by the primary dielectric constant measurement device 5a is input, and a primary controller 9 that controls the unvulcanizing compounding agent supply unit 7a. The primary dielectric constant measurement device 5a is intended to inspect the primary rubber material R1 just extruded by the extruder 3. The primary calculator 6a is connected to the primary controller 9 in a wired or wirelessly manner.

In this embodiment, one controller 9 is shared by the primary controller 9 and the final controller 9, but the controllers may be individually provided. In addition, in this embodiment, the primary calculator 6a and the final calculator 6b are separately provided, but one calculator may be shared. Alternatively, the primary calculator 6a, the final calculator 6b, and the controller 9 may be integrated into a single computer, for example.

In addition, in the present technology, to produce the primary rubber material R1, various kneading means (for example, a mixer) capable of mixing the unvulcanized rubber M and the unvulcanizing compounding agent Ac of predetermined type to produce the primary rubber material R1 may be used in place of the extruder 3. In this embodiment, one monitor 8 connected to the controller 9 in a wired or wirelessly manner is provided. In the configuration in which the primary controller 9 and the final controller 9 are separately provided, the controllers may be connected to the primary monitor 8 and the final monitor 8, respectively.

The extruder 4 has the configuration described in the previous embodiment, and the sheet-like primary rubber material R1 is continuously fed into the cylinder 4a from the material feeding port 4b via the hopper 4d. In addition, the vulcanizing compounding agent As of predetermined type is continuously fed from the material feeding port 4b via the hopper 4d by the vulcanizing compounding agent supply unit 7b. The vulcanizing compounding agent As is set to be fed at a predetermined ratio preset for 100 weight parts of the unvulcanized rubber M.

The fed primary rubber material R1 and the vulcanizing compounding agent As move forward while being mixed and kneaded in the cylinder 4a by the rotating screw. Then, the final rubber material R2 formed into a sheet form is continuously extruded from the extrusion port 4c.

The final dielectric constant measurement device 5b may use equipment various known specifications. Preferable equipment is capable of irradiating the inspection target (final rubber material R2) with ultrasonic waves and detecting the dielectric constant in a non-contact manner. For example, the final dielectric constant measurement device 5b sequentially detects the dielectric constant in the range through which the final rubber material R2 passes while being extruded.

Not only a single but a plurality of final dielectric constant measurement devices 5b may be aligned in the width direction of the final rubber material R2. Alternatively, the final dielectric constant measurement device 5b may be configured to be movable in the width direction of the final rubber material R2. By employing these configurations, the substantially entire width of the final rubber material R2 can be inspected. The dielectric constant in a specific range in the width direction of the final rubber material R2 may be detected, but the dielectric constant is preferably detected over the entire width and the entire length of the final rubber material R2.

As illustrated in FIG. 2, correlation data between the compounding ratio of the vulcanizing compounding agent As of predetermined type in the final rubber material R2 and the dielectric constant of the final rubber material R2 are input to the final calculator 6b. The final calculator 6b calculates the compounding ratio D1 of the vulcanizing compounding agent As in the final rubber material R2 on the basis of the correlation data and the sequentially-input dielectric constant.

In this embodiment, as illustrated in FIG. 2, correlation data between the compounding ratio of the unvulcanizing compounding agent Ac of predetermined type in the primary rubber material R1 and the dielectric constant of the primary rubber material R1 is also input to the primary calculator 6a. According to the type of the compounding agents A (Ac, As), the correlation between the compounding ratio and the dielectric constant of the unvulcanized rubber material R mixed with the compounding agent A (which the dielectric constant increases or decreases proportionally, the degree of change in the dielectric constant) varies, and therefore, for each compounding agent A, the correlation data is previously acquired and input to the primary calculator 6a or the final calculator 6b.

A compounding vulcanizing reference range C1 indicating the appropriate compounding ratio for each type of the vulcanizing compounding agent As is also input to the final calculator 6b. As illustrated in FIG. 3, the final calculator 6b sequentially compares the calculated compounding ratio D1 with the vulcanizing compounding reference range C1, and sequentially determines whether or not the compounding ratio D1 is within the vulcanizing compounding reference range C1.

The final controller 9 controls the vulcanizing compounding agent supply unit 7b based on comparison between the calculated compounding ratio D1 and a vulcanizing compounding reference range C21. Under this control, the ratio of the vulcanizing compounding agent As fed into the extruder 4 to the unvulcanized rubber M is adjusted such that the compounding ratio D1 of the vulcanizing compounding agent As, which is calculated by the final calculator 6b, is within the preset vulcanizing compounding reference range C1.

The determination result of the final calculator 6b is sequentially displayed on the monitor 8. The displayed determination result may be a warning simply indicating that the calculated compounding ratio D1 is out of the range of the vulcanizing compounding reference range C1, or a change in the compounding ratio D1 over time illustrated in FIG. 4 may be sequentially displayed.

As described above, according to the present technology, by detecting the dielectric constant of the final rubber material R2 and performing calculation based on the detected dielectric constant to calculate the compounding ratio of the vulcanizing compounding agent As in the final rubber material R2, the acceptability of the compounding ratio can be determined easily and rapidly by the non-destructive inspection. Therefore, by adjusting the ratio of the vulcanizing compounding agent As fed into the extruder 4 to the unvulcanized rubber M based on the determination result, it possible to obtain the final rubber material R2 in which the vulcanizing compounding agent As is mixed with the unvulcanized rubber M at an appropriate compounding ratio within the vulcanizing compounding reference range C1. Moreover, since the acceptability of the compounding ratio may be determined on the production line of the unvulcanized rubber material R, the final rubber material R2 of predetermined quality may be produced with good productivity.

As described in the previous embodiments, it is more preferable to determine the acceptability of the dispersion of the vulcanizing compounding agent As as well. That is, the extruded final rubber material R2 is divided into multiple segments in a plan view, and the dielectric constant is detected for each divided segment. Then, based on the magnitude of a variation in the detected dielectric constants of the segments, the final calculator 6b calculates a degree of dispersion D2 of the vulcanizing compounding agent As in the final rubber material R2.

A vulcanizing dispersion reference range C2 indicating the appropriate degree of dispersion D2 for each type of the vulcanizing compounding agent As is input to the final calculator 6b. Then, the final calculator 6b sequentially compares the calculated degree of dispersion D2 with the vulcanizing dispersion reference range C2 to determine whether or not the degree of dispersion D2 is within the vulcanizing dispersion reference range C2. Specifically, the degree of dispersion D2 described in the previous embodiment may be used. Then, the acceptability of the dispersion is determined based on the degree of dispersion D2.

The determination result of the final calculator 6b is sequentially displayed on the monitor 8. The displayed determination result may be a warning that simply indicates that the calculated degree of dispersion D2 is outside the range of the vulcanizing dispersion reference range C2, but as illustrated in FIG. 4, the dispersion of the dielectric constant (or the compounding ratio D2) may be displayed. Then, the contents described in the previous embodiment are displayed on the monitor 8.

When the final rubber material R2 includes a portion having an inadequate compounding ratio or the dispersion, the portion may be removed by a cutting machine such as a cutter installed on the production line. As a result, only the final rubber material R2 that satisfy predetermined quality is transported to the subsequent step of the production line, and the final rubber material R2 that satisfies the predetermined quality is excluded from the production line.

The contents described above may be applied to the primary rubber material R1 as well. In other words, by detecting the dielectric constant of the primary rubber material R1 and performing calculation based on the detected dielectric constant, the compounding ratio of the unvulcanizing compounding agent Ac in the primary rubber material R1 may be calculated to rapidly determine the acceptability of the compounding ratio. By adjusting the ratio of the unvulcanizing compounding agent Ac fed into the extruder 3 to the unvulcanized rubber M based on this determination result, it is possible to obtain the primary rubber material R1 in which the unvulcanizing compounding agent Ac is mixed with the unvulcanized rubber M at an appropriate compounding ratio within the unvulcanizing compounded reference range. Additionally, the acceptability of the dispersion of the unvulcanizing compounding agent Ac in the primary rubber material R1 may be determined in the same manner as in the final rubber material R2.

The invention claimed is:

1. A production method for producing a final rubber material, the method comprising:
   feeding a primary rubber material that is a mixture of unvulcanized rubber and an unvulcanizing compounding agent of predetermined type, and a vulcanizing compounding agent of predetermined type into an extruder;
   mixing the primary rubber material and the vulcanizing compounding agent in the extruder to continuously produce a final rubber material;
   calculating a compounding ratio of the vulcanizing compounding agent to the final rubber material by a final calculator based on a dielectric constant of the final rubber material extruded from the extruder; and
   adjusting a ratio of the vulcanizing compounding agent fed to the extruder to the unvulcanized rubber such that the calculated compounding ratio is within a preset vulcanizing compounding reference range.

2. The production method according to claim 1, further comprising:
   dividing the final rubber material into multiple segments in a plan view and detecting the dielectric constant for each of the segments;
   calculating a degree of dispersion of the vulcanizing compounding agent in the final rubber material by the final calculator based on a magnitude of a variation in the detected dielectric constants in the segments; and
   determining whether or not the calculated degree of dispersion of the vulcanizing compounding agent is within a preset vulcanizing dispersion reference range.

3. The production method according to claim 2, further comprising:
   categorizing the segments into a plurality of ranks by the final calculator based on a magnitude of the dielectric constants of the segments, and displaying the segments on a final monitor such that the respective categorized ranks are distinguishable.

4. The production method according to claim 1, further comprising:
   feeding the unvulcanized rubber and the unvulcanizing compounding agent into a kneading means other than the extruder and performing mixing to continuously produce primary rubber material;
   calculating a compounding ratio of the unvulcanizing compounding agent to the primary rubber material by a primary calculator based on a dielectric constant of the primary rubber material; and
   adjusting a ratio of the unvulcanizing compounding agent fed to the kneading means to the unvulcanized rubber such that the calculated compounding ratio of the unvulcanizing compounding agent is within a preset unvulcanizing compounded reference range.

5. The production method according to claim 3, further comprising:
   feeding the unvulcanized rubber and the unvulcanizing compounding agent into a kneading means other than the extruder and performing mixing to continuously produce primary rubber material;
   calculating the compounding ratio of the unvulcanizing compounding agent to the primary rubber material by a primary calculator based on a dielectric constant of the primary rubber material; and adjusting a ratio of the unvulcanizing agent fed to the kneading means to the unvulcanized rubber such that the calculated compounding ratio of the unvulcanizing compounding agent is within a present unvulcanizing compounded reference range.

\* \* \* \* \*